United States Patent [19]

Schwing et al.

[11] 4,301,286
[45] Nov. 17, 1981

[54] HERBICIDAL O-ALKYL SULFONYLISOUREAS

[75] Inventors: Gregory W. Schwing, Lincoln University, Pa.; Thomas S. Woods, Wilmington, Del.

[73] Assignee: E. I. Du Pont de Nemours and Company, Wilmington, Del.

[21] Appl. No.: 67,787

[22] Filed: Aug. 20, 1979

[51] Int. Cl.³ .................. C07D 251/42; C07D 251/46; C07D 401/12; C07D 413/12

[52] U.S. Cl. .................................... 544/211; 544/113

[58] Field of Search ........................ 544/211, 212, 113

[56] References Cited

U.S. PATENT DOCUMENTS 4,127,405  11/1978  Levitt .................................. 544/211

*Primary Examiner*—John M. Ford

[57] ABSTRACT

This invention relates to herbicidal O-alkyl sulfonylisoureas which are useful as herbicides, both general and selective.

7 Claims, No Drawings

HERBICIDAL O-ALKYL SULFONYLISOUREAS

BACKGROUND OF THE INVENTION

This invention relates to O-alkyl sulfonylisoureas having agricultural activity and in particular herbicidal activity.

U.S. applications Nos. 824,805, filed Aug. 15, 1977 now U.S. Pat. No. 4,127,405 and 840,389, filed Oct. 6, 1977 now U.S. Pat. No. 4,169,719 disclose, inter alia, compounds of the following formula as herbicides:

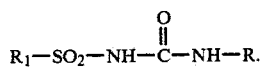

In the former, R is

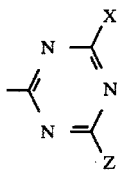

and in the latter, R is

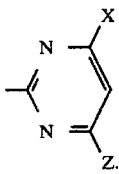

In each of those applications, $R_1$ may be

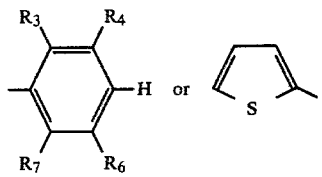

and $R_3$, $R_4$, $R_6$ and $R_7$ may each be hydrogen, fluorine, chlorine, bromine, or methyl. Moreover, in each application, each of $R_3$, $R_6$ and $R_7$ may be methoxy, and $R_3$ and $R_6$ may additionally be nitro, trifluoromethyl or $CH_3S(O)_n$-, (where n=1 or 2). In each application, X may be methyl, methoxy, ethoxy or methoxymethyl, and Z may be methyl or methoxy.

U.S. Pat. No. 3,637,366 discloses compounds having the formula:

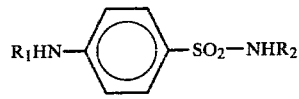

wherein
$R_1$ is hydrogen or lower saturated aliphatic acyl; and
$R_2$ is hydrogen, 2-pyrimidinyl, pyridyl, amidino, acetyl or carbamoyl.

The disclosed compounds are said to provide control of crabgrass, cress, endive, clover and Poa annua.

Substituted pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

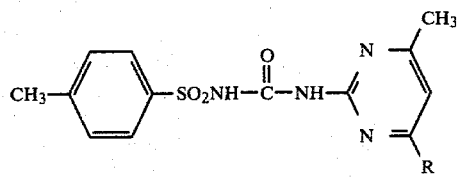

wherein
R=H or $CH_3$.

U.S. Pat. No. 3,823,007 discloses isourea salts as herbicides.

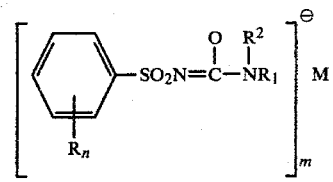

wherein
R is chloro, bromo, iodo, cyano, alkyl, alkoxy, nitro, amino or

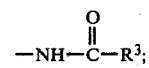

$R^3$ is hydrogen or alkyl;
n is the integer one to three;
m is the integer one or two;
M is of alkali metal, alkaline earth metal or ammonium;
$R^1$ and $R^2$ are each independently hydrogen, alkyl, alkoxy, alkynyl, phenyl, substituted phenyl having a maximum of three substituents said substituents being alkyl, bromine, chlorine, alkoxy, phenoxy, mono and dihalogenated phenoxy, said halogen being chlorine or bromine, or the group

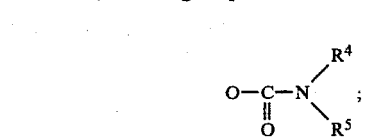

$R^4$ and $R^5$ are each independently hydrogen or alkyl.

U.S. Pat. No. 3,714,209 discloses the isopropylidine-aminoethanol salt of p-nitrobenzenesulfonylisourea as a herbicide:

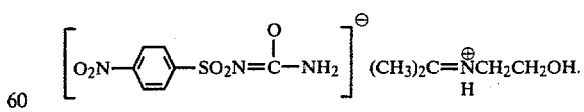

The presence of undesired vegetation causes substantial damage to useful crops, especially agricultural products that satisfy man's basic food needs, such as rice, corn, wheat, soybean and the like. The current population explosion and concomitant world food shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

According to this invention, there are provided novel compounds of formula I and their agriculturally suitable salts, suitable agricultural compositions containing them and methods of using them as general and selective herbicides having both pre-emergence and post-emergence activity and as plant growth modifiers:

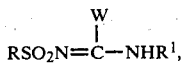

wherein

R is 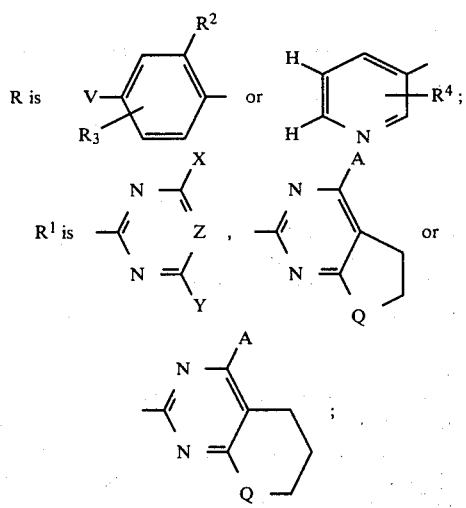

$R^2$ is $CH_3$, $OCH_3$, F, Cl, Br, $NO_2$, $CF_3$, $S(O)_mR^{10}$, where m is 0, 1 or 2, $COR^5$, or $SO_2NR^{10}R^{11}$;

$R^3$ is H, F, Cl, Br, $C_1$–$C_4$ alkyl, or $CH_3O$;

$R^4$ is Cl, Br, $CH_3$, $C_1$–$C_4$ alkoxy, $NO_2$, $CO_2R_6$, or $SCH_3$;

$R^5$ is $C_1$–$C_{10}$ alkoxy, $C_3$–$C_6$ alkenyloxy, $C_2$–$C_6$ alkoxy substituted with 1–3 halogens selected from F, Cl, or Br, $C_5$–$C_6$ cycloalkoxy, $OCH_2CH_2OR$, $O(CH_2)_3OR$, $C_1$–$C_4$ alkylthio, $NR^8R^9$ or $N(OCH_3)CH_3$;

$R^6$ is $C_1$–$C_6$ alkyl;

$R^7$ is $CH_3$ or $C_2H_5$;

$R^8$ and $R^9$ are independently $C_1$–$C_4$ alkyl, or $R^8$ and $R^9$ can be taken together to be $(CH_2)_4$, $(CH_2)_5$, or $O(CH_2CH_2-)_2$;

$R^{10}$ and $R^{11}$ are independently $C_1$–$C_6$ alkyl, $C_3$–$C_4$ alkenyl, or $R^{10}$ and $R^{11}$ can be taken together to be $(CH_2)_4$, $(CH_2)_5$, or $O(CH_2CH_2-)_2$;

V is H or F;

W is Cl, Br or $OR^{12}$;

$R^{12}$ is $C_1$–$C_{12}$ alkyl, $C_3$–$C_4$ alkenyl, $CH_2CH_2OCH_3$, $CH_2CH_2OCH_2CH_3$, $(CH_2)_3OCH_3$, benzyl, $CHR^{13}CO_2R^{14}$, where $R^{13}$ is H or $CH_3$ and $R^{14}$ is $C_1$–$C_4$ alkyl;

X is $CH_3$ or $OCH_3$;

Y is $CH_3$, $C_1$–$C_4$ alkoxy, $O(CH_2)_nOR^{15}$, where n is 1–3 and $R^{15}$ is $C_1$–$C_3$ alkyl; $OCHR^{16}CO_2R^{15}$, where $R^{16}$ is H or $CH_3$, $CF_3CH_2O$ or $CCl_3CH_2O$;

Z is N or CH;

Q is $CH_2$ or O; and

A is $CH_3$ or $CH_3O$ and their agriculturally acceptable salts, provided that when $R^1$ is

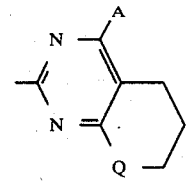

then $R^2$ is $COR^5$ and $R^4$ is other than H.

Preferred for reasons of ease of isolation are those compounds of formula I wherein W is $OR^{12}$.

More preferred for reasons of ease of synthesis are:

(1) Compounds of the Preferred scope wherein

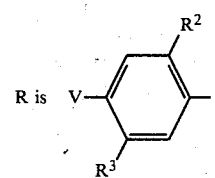

and V is H.

(2) Compounds of the More Preferred (1) wherein

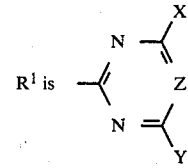

(3) Compounds of the More Preferred (2) wherein $R^2$ is Cl, $CH_3$, $OCH_3$, $COR^5$, $SO_2NR^{10}R^{11}$, $SO_2R^{10}$ or $NO_2$.

(4) Compounds of the More Preferred (3) wherein $R^3$ is H, Cl, $CH_3$ or $OCH_3$.

Still More Preferred for reasons of biological activity or ease of synthesis, or both, are those compounds of the More Preferred (4) wherein $R^2$ is Cl, $NO_2$ or $COR^5$, where $R_5$ is $C_1$–$C_3$ alkoxy or allyloxy.

Specifically preferred is N'-(2-chlorophenylsulfonyl)-N-(4-methoxy-6-methyl-1,3,5-triazin-2-yl)-carbamimidic acid, methyl ester.

DETAILED DESCRIPTION

Synthesis

Compounds of Formula I in which W is Cl, Br, or $OR^{12}$ may be prepared by sequence of reactions shown in Equation 1.

Equation 1

-continued

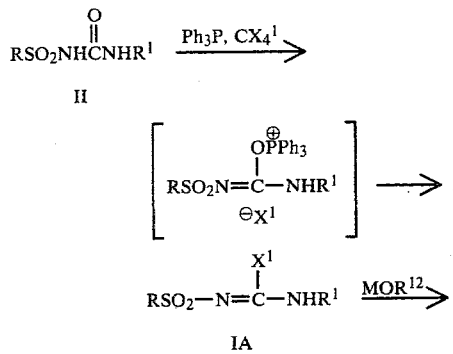

wherein

R, $R^1$ and $R^{12}$ are as previously defined in the broadest scope;

$X^1$ is Cl or Br; and

M is Na, K or Li.

The synthesis of the compounds of Formula II, which are the starting materials for Equation 1 is described in U.S. Pat. No. 4,127,405.

The compounds of Formula IA are prepared by adding the appropriate carbon tetrahalide to a solution of one of the compounds of Formula II and triphenyl phosphine in an inert aprotic solvent such as acetonitrile at about $-10°$ to $25°$. The reaction is completed by stirring at the designated temperature for 10 to 48 hours. The carbamimidoyl halides of Formula IA may be isolated by passing the reaction solution through a silica gel column to remove the triphenyl phosphine oxide and then removing the solvent by evaporation under reduced pressure.

The compounds of Formula IA may also be converted directly to the compounds of Formula IB by reacting the reaction mixture with a metal alkoxide at $-10°$ to $25°$. The reaction is completed by stirring at ambient temperature for 2 to 24 hours. The crude products of Formula IB are isolated by filtering off the precipitated metal halide and removing the solvent by evaporation under reduced pressure. Further purification may be accomplished by recrystallization or by column chromatography over silica gel.

It will be understood by one skilled in the art that the compounds of Formula IA are not necessarily converted directly to the compounds of Formula IB, but may first form the carbodiimides of Formula III.

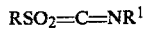

Many compounds, particularly compounds in which the heterocyclic moiety is pyrimidinyl, may be prepared by the sequence of reactions shown in Equation 2.

Equation 2

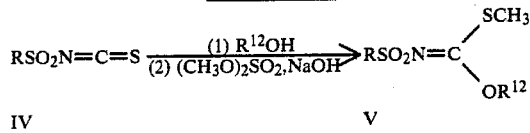

-continued
Equation 2

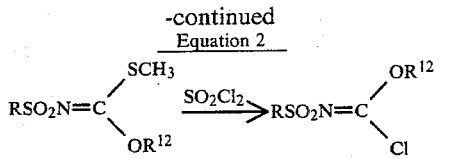

The compounds of Formula V are known in the art and their preparation is described by R. Gompper and W. Hägele in Chemische Berichte 99, 2885–2899 (1966), the contents of which are herein incorporated by reference.

The compounds of Formula VI are prepared by treating the compounds of Formula V with sulfuryl chloride in an inert organic solvent such as methylene chloride or chloroform at temperatures between about $-10°$ and $80°$. The compounds of Formula VI are isolated by removing the solvent under reduced pressure, and may be passed on to the next step without further purification.

The compounds of Formula VI are converted to the compounds of Formula IB in the following manner. First, the lithium salt of the 2-aminoheterocycle is prepared by reacting the aminoheterocycle with n-butyl lithium in a solvent such as tetrahydrofuran. To this salt solution is added a solution of the compound of Formula VI in tetrahydrofuran at a temperature of about $-10°$ to $10°$. The reaction mixture is then stirred at about $0°$–$10°$ for about $\frac{1}{2}$–2 hours and at ambient temperature for about $\frac{1}{2}$–4 hours. The products of Formula IB are isolated by filtering off the inorganic salts and removing the solvent under reduced pressure. The products may be further purified by recrystallization or by column chromatography on silica gel using a suitable eluent such as ethyl acetate.

In the following examples, all parts are by weight and all temperatures in ° C. unless otherwise indicated.

EXAMPLE 1

N'-(2-Chlorophenylsulfonyl)-N-(4-methoxy-6-methyl-1,3,5-triazin-2-yl)carbamimidic acid, methyl ester To a solution of 7.2 g. of 2-chloro[(4-methoxy-6-methyl-1,3,5-triazin-2-yl)aminocarbonyl]benzenesulfonamide, and 6.3 g of triphenyl phosphine in 50 ml of acetonitrile (dried by passing through $Al_2O_3$) which was cooled to $0°$ was added 3.1 g of carbon tetrachloride all at once. The resulting solution was stirred at $0°$–$5°$ for 2 hours and at ambient temperature for 20 hours. The carbamimidoyl chloride was not isolated but was immediately reacted with sodium methoxide in the following manner. The solution was cooled to $-5°$ and 1.1 g of sodium methoxide added in one portion. The solution was stirred at $0°$–$5°$ for 2 hours and at ambient temperature for 20 hours. The resulting precipitated sodium chloride was filtered off and the filtrate stripped to give an oily residue. Chromatography of the filtrate on a silica column using chloroform as the eluent gave 1.8 g of crude product as a sticky tan solid. Recrystallization from a mixture of 30 ml of 1-chlorobutane and 5 ml of chloroform gave 1.3 g of N'-(2-chlorophenylsulfonyl)-N-(4-methoxy-6-methyl-1,3,5-triazin-2-yl)carbamimidic acid, methyl ester, m.p. 156°–157°.

Anal. Calcd. for $C_{13}H_{14}ClN_5O_4S$:
C, 41.99; H, 3.80; N, 18.84; S, 8.62.
Found: C, 42.6, 42.5; H, 3.96, 3.98; N, 19.5, 19.6; S, 8.66.

NMR $(CDCl_3)\delta$: 2.5(S, 3H, Het—$CH_3$); ~4.0(two singlets, 6H, $OCH_3$'s); 7.3–8.4(m, 4H, 4 aromatics); ~10.2 (broad, 1H, NH).

EXAMPLE 2

Methyl N-(2-methylphenylsulfonyl)carbonimidochloridate

To 6.8 g of O-methyl S-methyl N-(2-methylphenylsulfonyl)carbonimidothioate in 20 ml of methylene chloride is added 6.8 g of sulfuryl chloride. The reaction mixture is stirred under a nitrogen atmosphere at ambient temperature for 2 hours, and then refluxed for an additional 2 hours. Removal of the solvent under reduced pressure gives 5.0 g of methyl N-(2-methylphenylsulfonyl)carbonimidochloridate as a light yellow oil. This product is used without further purification in the reaction described in Example 3.

EXAMPLE 3

N'-(2-Methylphenylsulfonyl)-N-(4,6-dimethylpyrimidin-2-yl)carbamimidic acid, methyl ester To 1.2 g of 2-amino-4,6-dimethylpyrimidine in 50 ml of tetrahydrofuran is added 6.85 ml of 1.6 molar n-butyl lithium in hexane at 0°. The mixture is stirred for 15 minutes. To this solution is added dropwise, a solution of 2.1 g of methyl N-(2-methylphenylsulfonyl)carbonimidochloridate in 5 ml of tetrahydrofuran at 0°–10°. This reaction mixture is stirred for 30 minutes at 0°–10° and 30 minutes at ambient temperature. The reaction mixture is filtered and the solvent is stripped from the filtrate under reduced pressure to yield a crude product. The crude product is further purified via dry column chromatography on silica gel with ethyl acetate as the eluent. Pure N'-(2-methylphenylsulfonyl)-N-(4,6-dimethylpyrimidin-2-yl)carbamimidic acid, methyl ester is obtained.

Using the methods and examples discussed above, the compounds described in Tables I–IX can be prepared by one skilled in the art.

TABLE I

| V | $R_2$ | $R_3$ | W | X | Y | m.p. |
|---|---|---|---|---|---|---|
| H | —$CO_2CH_3$ | H | Cl | $CH_3$ | $CH_3O$ | |
| H | —$CO_2CH_3$ | H | Br | $CH_3$ | $CH_3O$ | |
| H | —$CO_2CH_3$ | H | $OCH_3$ | $CH_3$ | $CH_3O$ | |
| H | —$CO_2CH_3$ | H | $OC_2H_5$ | $CH_3$ | $CH_3O$ | |
| H | —$CO_2CH_3$ | H | O—i-$C_3H_7$ | $CH_3$ | $CH_3O$ | |
| H | —$CO_2CH_3$ | H | O—n-$C_6H_{13}$ | $CH_3$ | $CH_3O$ | |
| H | —$CO_2CH_3$ | H | O—n-$C_{12}H_{25}$ | $CH_3$ | $CH_3O$ | |
| H | —$CO_2CH_3$ | H | O—$CH_2CH=CH_2$ | $CH_3$ | $CH_3O$ | |
| H | —$CO_2CH_3$ | H | $OCH_2CH=CHCH_3$ | $CH_3$ | $CH_3O$ | |
| H | —$CO_2CH_3$ | H | $O(CH_2)_2OCH_3$ | $CH_3$ | $CH_3O$ | |
| H | —$CO_2CH_3$ | H | $O(CH_2)_2OC_2H_5$ | $CH_3$ | $CH_3O$ | |
| H | —$CO_2CH_3$ | H | $O(CH_2)_3OCH_3$ | $CH_3$ | $CH_3O$ | |
| H | —$CO_2CH_3$ | H | $OCH_2$—Ph | $CH_3$ | $CH_3O$ | |
| H | —$CO_2CH_3$ | H | $OCH_2CO_2CH_3$ | $CH_3$ | $CH_3O$ | |
| H | —$CO_2CH_3$ | H | $OCH(CH_3)CO_2CH_3$ | $CH_3$ | $CH_3O$ | |
| H | —$CO_2CH_3$ | H | $OCH_2CO_2C_2H_5$ | $CH_3$ | $CH_3O$ | |
| H | —$CO_2CH_3$ | H | $OCH(CH_3)CO_2$—i-$C_3H_7$ | $CH_3$ | $CH_3O$ | |
| F | $CO_2CH_3$ | H | O—i-$C_3H_7$ | $CH_3$ | $CH_3O$ | |
| H | $CO_2CH_3$ | 5-F | $OCH_3$ | $CH_3$ | $CH_3O$ | |
| H | $CO_2CH_3$ | 5-Cl | $OCH_3$ | $CH_3$ | $CH_3O$ | |
| H | $CO_2CH_3$ | 5-Br | $OCH_3$ | $CH_3$ | $CH_3O$ | |
| H | $CO_2CH_3$ | 5-$CH_3$ | $OCH_3$ | $CH_3$ | $CH_3O$ | |
| H | $CO_2CH_3$ | 5-i-$C_3H_7$ | $OCH_3$ | $CH_3$ | $CH_3O$ | |
| H | $CO_2CH_3$ | 5-n-$C_4H_9$ | $OCH_3$ | $CH_3$ | $CH_3O$ | |
| H | $CO_2CH_3$ | 5-$OCH_3$ | $OCH_3$ | $CH_3$ | $CH_3O$ | |
| H | $CO_2CH_3$ | 6-Cl | $OCH_3$ | $CH_3$ | $CH_3O$ | |
| H | $CO_2CH_3$ | 3-Cl | $OCH_3$ | $CH_3$ | $CH_3O$ | |
| H | —$CO_2$—i-$C_3H_7$ | H | $OCH_3$ | $CH_3$ | $CH_3O$ | |
| H | —$CO_2$—n-$C_6H_{13}$ | H | $OCH_3$ | $CH_3$ | $CH_3O$ | |
| H | —$CO_2$—n-$C_{10}H_{21}$ | H | $OCH_3$ | $CH_3$ | $CH_3O$ | |
| H | —$CO_2CH_2CH=CH_2$ | H | $OCH_3$ | $CH_3$ | $CH_3O$ | |
| H | —$CO_2CH_2CH=CH—CH_3$ | H | $OCH_3$ | $CH_3$ | $CH_3O$ | |
| H | —$CO_2CH_2CH_2Cl$ | H | $OCH_3$ | $CH_3$ | $CH_3O$ | |
| H | —$CO_2CH_2CH_2Br$ | H | $OCH_3$ | $CH_3$ | $CH_3O$ | |
| H | —$CO_2CH_2CF_3$ | H | $OCH_3$ | $CH_3$ | $CH_3O$ | |
| H | —$CO_2CH_2CHCl_2$ | H | $OCH_3$ | $CH_3$ | $CH_3O$ | |

TABLE I-continued

| V | R₂ | R₃ | W | X | Y | m.p. |
|---|---|---|---|---|---|---|
| H | —CO₂—⟨S⟩ (5-membered, thiophene) | H | OCH₃ | CH₃ | CH₃O | |
| H | —CO₂—⟨S⟩ (6-membered, thiopyran) | H | OCH₃ | CH₃ | CH₃O | |
| H | —CO₂CH₂CH₂OCH₃ | H | OCH₃ | CH₃ | CH₃O | |
| H | —CO₂CH₂CH₂OC₂H₅ | H | OCH₃ | CH₃ | CH₃O | |
| H | —COSCH₃ | H | OCH₃ | CH₃ | CH₃O | |
| H | —COS—i-C₃H₇ | H | OCH₃ | CH₃ | CH₃O | |
| H | —CON(CH₃)₂ | H | OCH₃ | CH₃ | CH₃O | |
| H | —CON(CH₃)(OCH₃) | H | OCH₃ | CH₃ | CH₃O | |
| H | —CON(pyrrolidinyl) | H | OCH₃ | CH₃ | CH₃O | |
| H | —CON(piperidinyl) | H | OCH₃ | CH₃ | CH₃O | |
| H | —CON(morpholinyl) | H | OCH₃ | CH₃ | CH₃O | |
| H | CH₃ | H | OCH₃ | CH₃ | OCH₃ | |
| H | CH₃O | H | OCH₃ | CH₃ | OCH₃ | |
| H | F | H | OCH₃ | CH₃ | OCH₃ | |
| H | Br | H | OCH₃ | CH₃ | OCH₃ | |
| H | NO₂ | H | OCH₃ | CH₃ | OCH₃ | |
| H | CF₃ | H | OCH₃ | CH₃ | OCH₃ | |
| H | SCH₃ | H | OCH₃ | CH₃ | OCH₃ | |
| H | SOCH₃ | H | OCH₃ | CH₃ | OCH₃ | |
| H | SO₂CH₃ | H | OCH₃ | CH₃ | OCH₃ | |
| H | SO₂N(CH₃)₂ | H | OCH₃ | CH₃ | OCH₃ | |
| H | SO₂N(C₂H₅)₂ | H | OCH₃ | CH₃ | OCH₃ | |
| H | SO₂N(n-C₆H₁₃)₂ | H | OCH₃ | CH₃ | OCH₃ | |
| H | SO₂N(CH₂CH=CH₂)₂ | H | OCH₃ | CH₃ | OCH₃ | |
| H | SO₂N(CH₂CH=CHCH₃)₂ | H | OCH₃ | CH₃ | OCH₃ | |
| H | SO₂N(pyrrolidinyl) | H | OCH₃ | CH₃ | OCH₃ | |
| H | SO₂N(piperidinyl) | H | OCH₃ | CH₃ | OCH₃ | |
| H | SO₂N(morpholinyl) | H | OCH₃ | CH₃ | OCH₃ | |
| H | Cl | H | Cl | CH₃ | OCH₃ | |
| H | CH₃ | H | Cl | CH₃ | OCH₃ | |
| H | NO₂ | H | Cl | CH₃ | OCH₃ | |
| H | CF₃ | H | Cl | CH₃ | OCH₃ | |
| H | SO₂CH₃ | H | Cl | CH₃ | OCH₃ | |
| H | SO₂N(CH₃)₂ | H | Cl | CH₃ | OCH₃ | |
| H | CH₃O | H | Cl | CH₃ | OCH₃ | |
| H | —CO₂CH₃ | H | OCH₃ | CH₃ | CH₃ | |
| H | —CO₂CH₃ | H | OCH₃ | CH₃ | —OCH₂CH₃ | |
| H | —CO₂CH₃ | H | OCH₃ | CH₃ | —O—n-C₄H₉ | |
| H | —CO₂CH₃ | H | OCH₃ | CH₃ | —OCH₂OCH₃ | |
| H | —CO₂CH₃ | H | OCH₃ | CH₃ | O—CH₂O—i-C₃H₇ | |
| H | —CO₂CH₃ | H | OCH₃ | CH₃ | —O(CH₂)₂OCH₃ | |
| H | —CO₂CH₃ | H | OCH₃ | CH₃ | —O(CH₂)₃OCH₃ | |
| H | —CO₂CH₃ | H | OCH₃ | CH₃ | —OCH₂CO₂CH₃ | |
| H | —CO₂CH₃ | H | OCH₃ | CH₃ | —OCH(CH₃)CO₂CH₃ | |

TABLE I-continued

| V | R₂ | R₃ | W | X | Y | m.p. |
|---|---|---|---|---|---|---|
| H | —CO₂CH₃ | H | OCH₃ | CH₃ | —OCH₂CO₂Et | |
| H | —CO₂CH₃ | H | OCH₃ | CH₃ | —OCH₂CO₂—i-C₃H₇ | |
| H | —CO₂CH₃ | H | OCH₃ | CH₃ | —OCH₂CCl₃ | |
| H | —CO₂CH₃ | H | OCH₃ | CH₃ | —OCH₂CF₃ | |
| H | —CO₂CH₃ | H | OCH₃ | CH₃O | —OCH₂CF₃ | |
| H | —CO₂CH₃ | H | OCH₃ | CH₃O | CH₃O | |
| H | Cl | H | O—i-C₃H₇ | CH₃ | CH₃O | |
| H | CH₃ | H | O—i-C₃H₇ | CH₃ | CH₃O | |
| H | NO₂ | H | O—i-C₃H₇ | CH₃ | CH₃O | |
| H | CF₃ | H | O—i-C₃H₇ | CH₃ | CH₃O | |
| H | SO₂CH₃ | H | O—i-C₃H₇ | CH₃ | CH₃O | |
| H | SO₂N(CH₃)₂ | H | O—i-C₃H₇ | CH₃ | CH₃O | |
| H | CH₃O | H | O—i-C₃H₇ | CH₃ | CH₃O | |

TABLE II

| V | R₂ | R₃ | W | X | Y | m.p. |
|---|---|---|---|---|---|---|
| H | —CO₂CH₃ | H | Cl | CH₃O | CH₃O | |
| H | —CO₂CH₃ | H | Cl | CH₃ | CH₃O | |
| H | —CO₂CH₃ | H | Br | CH₃ | CH₃O | |
| H | —CO₂CH₃ | H | OCH₃ | CH₃ | CH₃O | |
| H | —CO₂CH₃ | H | OC₂H₅ | CH₃ | CH₃O | |
| H | —CO₂CH₃ | H | O—i-C₃H₇ | CH₃ | CH₃O | |
| H | —CO₂CH₃ | H | O—n-C₆H₁₃ | CH₃ | CH₃O | |
| H | —CO₂CH₃ | H | O—n-C₁₂H₂₅ | CH₃ | CH₃O | |
| H | —CO₂CH₃ | H | OCH₂CH=CH₂ | CH₃ | CH₃O | |
| H | —CO₂CH₃ | H | OCH₂CH=CHCH₃ | CH₃ | CH₃O | |
| H | —CO₂CH₃ | H | O(CH₂)₂OCH₃ | CH₃ | CH₃O | |
| H | —CO₂CH₃ | H | O(CH₂)₂OC₂H₅ | CH₃ | CH₃O | |
| H | —CO₂CH₃ | H | O(CH₂)₃OCH₃ | CH₃ | CH₃O | |
| H | —CO₂CH₃ | H | OCH₂—C₆H₅ | CH₃ | CH₃O | |
| H | —CO₂CH₃ | H | OCH₂CO₂CH₃ | CH₃ | CH₃O | |
| H | —CO₂CH₃ | H | OCH(CH₃)CO₂CH₃ | CH₃ | CH₃O | |
| H | —CO₂CH₃ | H | OCH₂CO₂C₂H₅ | CH₃ | CH₃O | |
| H | —CO₂CH₃ | H | OCH(CH₃)CO₂—i-C₃H₇ | CH₃ | CH₃O | |
| F | —CO₂CH₃ | H | O—i-C₃H₇ | CH₃ | CH₃O | |
| H | —CO₂CH₃ | 5-F | OCH₃ | CH₃ | CH₃O | |
| H | —CO₂CH₃ | 5-Cl | OCH₃ | CH₃ | CH₃O | |
| H | —CO₂CH₃ | 5-Br | OCH₃ | CH₃ | CH₃O | |
| H | —CO₂CH₃ | 5-CH₃ | OCH₃ | CH₃ | CH₃O | |
| H | —CO₂CH₃ | 5-i-C₃H₇ | OCH₃ | CH₃ | CH₃O | |
| H | —CO₂CH₃ | 5-n-C₄H₉ | OCH₃ | CH₃ | CH₃O | |
| H | CO₂CH₃ | 5-OCH₃ | OCH₃ | CH₃ | CH₃O | |
| H | CO₂CH₃ | 6-Cl | OCH₃ | CH₃ | CH₃O | |
| H | CO₂CH₃ | 3-Cl | OCH₃ | CH₃ | CH₃O | |
| H | CO₂—i-C₃H₇ | H | OCH₃ | CH₃ | CH₃O | |
| H | CO₂—n-C₆H₁₃ | H | OCH₃ | CH₃ | CH₃O | |
| H | CO₂—n-C₁₀H₂₁ | H | OCH₃ | CH₃ | CH₃O | |
| H | CO₂CH₂CH=CH₂ | H | OCH₃ | CH₃ | CH₃O | |
| H | CO₂CH₂CH=CHCH₃ | H | OCH₃ | CH₃ | CH₃O | |
| H | CO₂CH₂CH₂Cl | H | OCH₃ | CH₃ | CH₃O | |
| H | CO₂CH₂CH₂Br | H | OCH₃ | CH₃ | CH₃O | |
| H | CO₂CH₂CF₃ | H | OCH₃ | CH₃ | CH₃O | |
| H | CO₂CH₂CHCl₂ | H | OCH₃ | CH₃ | CH₃O | |

TABLE II-continued

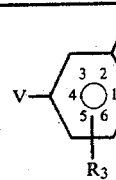

| V | R₂ | R₃ | W | X | Y | m.p. |
|---|---|---|---|---|---|---|
| H | CO₂-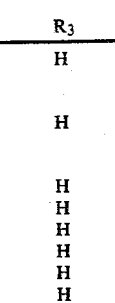 (S, 5-ring) | H | OCH₃ | CH₃ | CH₃O | |
| H | CO₂-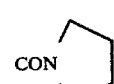 (S, 6-ring) | H | OCH₃ | CH₃ | CH₃O | |
| H | CO₂CH₂CH₂OCH₃ | H | OCH₃ | CH₃ | CH₃O | |
| H | CO₂CH₂CH₂OC₂H₅ | H | OCH₃ | CH₃ | CH₃O | |
| H | COSCH₃ | H | OCH₃ | CH₃ | CH₃O | |
| H | COS—i-C₃H₇ | H | OCH₃ | CH₃ | CH₃O | |
| H | CON(CH₃)₂ | H | OCH₃ | CH₃ | CH₃O | |
| H | CON(CH₃)OCH₃ | H | OCH₃ | CH₃ | CH₃O | |
| H | CON-pyrrolidine 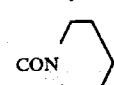 | H | OCH₃ | CH₃ | CH₃O | |
| H | CON-piperidine 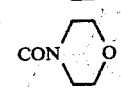 | H | OCH₃ | CH₃ | CH₃O | |
| H | CON-morpholine 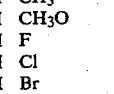 | H | OCH₃ | CH₃ | CH₃O | |
| H | CH₃ | H | OCH₃ | CH₃ | OCH₃ |  |
| H | CH₃O | H | OCH₃ | CH₃ | OCH₃ |  |
| H | F | H | OCH₃ | CH₃ | OCH₃ |  |
| H | Cl | H | OCH₃ | CH₃ | OCH₃ |  |
| H | Br | H | OCH₃ | CH₃ | OCH₃ |  |
| H | NO₂ | H | OCH₃ | CH₃ | OCH₃ |  |
| H | CF₃ | H | OCH₃ | CH₃ | OCH₃ |  |
| H | SCH₃ | H | OCH₃ | CH₃ | OCH₃ |  |
| H | SOCH₃ | H | OCH₃ | CH₃ | OCH₃ |  |
| H | SO₂CH₃ | H | OCH₃ | CH₃ | OCH₃ |  |
| H | SO₂N(CH₃)₂ | H | OCH₃ | CH₃ | OCH₃ |  |
| H | SO₂N(C₂H₅)₂ | H | OCH₃ | CH₃ | OCH₃ |  |
| H | SO₂N(n-C₆H₁₃)₂ | H | OCH₃ | CH₃ | OCH₃ |  |
| H | SO₂N(CH₂CH=CH₂)₂ | H | OCH₃ | CH₃ | OCH₃ |  |
| H | SO₂N(CH₂CH=CHCH₃)₂ | H | OCH₃ | CH₃ | OCH₃ |  |
| H | SO₂N-pyrrolidine  | H | OCH₃ | CH₃ | OCH₃ |  |
| H | SO₂N-piperidine 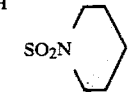 | H | OCH₃ | CH₃ | OCH₃ |  |
| H | SO₂N-morpholine 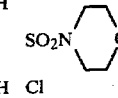 | H | OCH₃ | CH₃ | OCH₃ |  |
| H | Cl | H | Cl | CH₃ | OCH₃ |  |
| H | CH₃ | H | Cl | CH₃ | OCH₃ |  |
| H | CH₃O | H | Cl | CH₃ | OCH₃ |  |
| H | NO₂ | H | Cl | CH₃ | OCH₃ |  |
| H | CF₃ | H | Cl | CH₃ | OCH₃ |  |
| H | SO₂CH₃ | H | Cl | CH₃ | OCH₃ |  |
| H | SO₂N(CH₃)₂ | H | Cl | CH₃ | OCH₃ |  |
| H | —CO₂CH₃ | H | OCH₃ | CH₃ | CH₃ |  |
| H | —CO₂CH₃ | H | OCH₃ | CH₃ | OCH₂CH₃ |  |
| H | —CO₂CH₃ | H | OCH₃ | CH₃ | O—n-C₄H₉ |  |
| H | —CO₂CH₃ | H | OCH₃ | CH₃ | OCH₂OCH₃ |  |
| H | —CO₂CH₃ | H | OCH₃ | CH₃ | OCH₂O—i-C₃H₇ |  |
| H | —CO₂CH₃ | H | OCH₃ | CH₃ | O(CH₂)₂OCH₃ |  |
| H | —CO₂CH₃ | H | OCH₃ | CH₃ | O(CH₂)₃OCH₃ |  |

TABLE II-continued

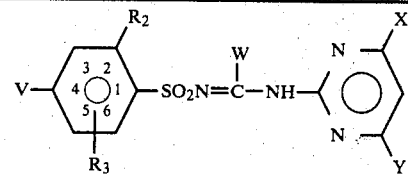

| V | R₂ | R₃ | W | X | Y | m.p. |
|---|---|---|---|---|---|---|
| H | —CO$_2$CH$_3$ | H | OCH$_3$ | CH$_3$ | OCH$_2$CO$_2$CH$_3$ | |
| H | —CO$_2$CH$_3$ | H | OCH$_3$ | CH$_3$ | OCHCO$_2$CH$_3$<br>\|<br>CH$_3$ | |
| H | —CO$_2$CH$_3$ | H | OCH$_3$ | CH$_3$ | OCH$_2$CH$_2$Et | |
| H | —CO$_2$CH$_3$ | H | OCH$_3$ | CH$_3$ | OCH$_2$CO$_2$—i-C$_3$H$_7$ | |
| H | —CO$_2$CH$_3$ | H | OCH$_3$ | CH$_3$ | OCH$_2$CCl$_3$ | |
| H | —CO$_2$CH$_3$ | H | OCH$_3$ | CH$_3$ | OCH$_2$CF$_3$ | |
| H | —CO$_2$CH$_3$ | H | OCH$_3$ | CH$_3$O | OCH$_2$CF$_3$ | |
| H | Cl | H | O—i-C$_3$H$_7$ | CH$_3$ | CH$_3$O— | |
| H | CH$_3$ | H | O—i-C$_3$H$_7$ | CH$_3$ | CH$_3$O— | |
| H | NO$_2$ | H | O—i-C$_3$H$_7$ | CH$_3$ | CH$_3$O— | |
| H | CF$_3$ | H | O—i-C$_3$H$_7$ | CH$_3$ | CH$_3$O— | |
| H | SO$_2$CH$_3$ | H | O—i-C$_3$H$_7$ | CH$_3$ | CH$_3$O— | |
| H | SO$_2$N(CH$_3$)$_2$ | H | O—i-C$_3$H$_7$ | CH$_3$ | CH$_3$O— | |
| H | SO$_2$N(C$_2$H$_5$)$_2$ | H | O—i-C$_3$H$_7$ | CH$_3$ | CH$_3$O— | |
| H | CH$_3$O | H | O—i-C$_3$H$_7$ | CH$_3$ | CH$_3$O— | |
| H | SCH$_3$ | H | O—i-C$_3$H$_7$ | CH$_3$ | CH$_3$O— | |
| H | SOCH$_3$ | H | O—i-C$_3$H$_7$ | CH$_3$ | CH$_3$O— | |

TABLE III

| V | R₂ | R₃ | W | A | Q | m.p. |
|---|---|---|---|---|---|---|
| H | Cl | H | OCH$_3$ | CH$_3$ | —CH$_2$— | |
| H | Cl | H | OCH$_3$ | OCH$_3$ | —CH$_2$— | |
| H | Cl | H | Cl | OCH$_3$ | —CH$_2$— | |
| H | CO$_2$CH$_3$ | H | OCH$_3$ | OCH$_3$ | —CH$_2$— | |
| H | NO$_2$ | H | OCH$_3$ | OCH$_3$ | —CH$_2$— | |
| H | SO$_2$CH$_3$ | H | OCH$_3$ | OCH$_3$ | —CH$_2$— | |
| H | SO$_2$N(CH$_3$)$_2$ | H | OCH$_3$ | OCH$_3$ | —CH$_2$— | |
| H | CF$_3$ | H | OCH$_3$ | OCH$_3$ | —CH$_2$— | |
| H | Cl | H | OCH$_3$ | CH$_3$ | —O— | |
| H | CO$_2$CH$_3$ | H | OCH$_3$ | CH$_3$ | —O— | |
| H | NO$_2$ | H | OCH$_3$ | CH$_3$ | —O— | |
| H | SO$_2$CH$_3$ | H | OCH$_3$ | CH$_3$ | —O— | |
| H | SO$_2$N(CH$_3$)$_2$ | H | OCH$_3$ | CH$_3$ | —O— | |
| H | CF$_3$ | H | OCH$_3$ | CH$_3$ | —O— | |
| H | CO$_2$—< | H | OCH$_3$ | CH$_3$ | —CH$_2$— | |
| H | CO$_2$—< | H | OCH$_3$ | CH$_3$ | —O— | |

TABLE IV

| V | R₂ | R₃ | W | A | Q | m.p. |
|---|---|---|---|---|---|---|
| H | CO$_2$CH$_3$ | H | OCH$_3$ | CH$_3$ | —CH$_2$— | |
| H | CO$_2$CH$_3$ | H | OCH$_3$ | CH$_3$O | —CH$_2$— | |
| H | CO$_2$CH$_3$ | H | OCH$_3$ | CH$_3$O | —O— | |
| H | CO$_2$CH$_3$ | H | OCH$_3$ | CH$_3$ | —O— | |
| H | CO$_2$—< | H | OCH$_3$ | CH$_3$ | —CH$_2$— | |

TABLE IV-continued

| V | R₂ | R₃ | W | A | Q | m.p. |
|---|---|---|---|---|---|---|
| H | CO$_2$CH$_2$CH$_3$ | H | OCH$_3$ | CH$_3$ | —O— | |

TABLE V

| R₄ | W | X | Y | m.p. |
|---|---|---|---|---|
| 2-Cl | Cl | CH$_3$ | OCH$_3$ | |
| 2-Cl | Br | CH$_3$ | OCH$_3$ | |
| 2-Cl | OCH$_3$ | CH$_3$ | OCH$_3$ | |
| 4-Cl | OCH$_3$ | CH$_3$ | OCH$_3$ | |
| 2-Br | OCH$_3$ | CH$_3$ | OCH$_3$ | |
| 4-Br | OCH$_3$ | CH$_3$ | OCH$_3$ | |
| 2-CH$_3$ | OCH$_3$ | CH$_3$ | OCH$_3$ | |
| 4-CH$_3$ | OCH$_3$ | CH$_3$ | OCH$_3$ | |
| 2-OCH$_3$ | OCH$_3$ | CH$_3$ | OCH$_3$ | |
| 4-OCH$_3$ | OCH$_3$ | CH$_3$ | OCH$_3$ | |
| 2-O(CH$_2$)$_3$CH$_3$ | OCH$_3$ | CH$_3$ | OCH$_3$ | |
| 2-NO$_2$ | OCH$_3$ | CH$_3$ | OCH$_3$ | |
| 4-NO$_2$ | OCH$_3$ | CH$_3$ | OCH$_3$ | |
| 2-CO$_2$CH$_3$ | OCH$_3$ | CH$_3$ | OCH$_3$ | |
| 4-CO$_2$CH$_3$ | OCH$_3$ | CH$_3$ | OCH$_3$ | |
| 2-SCH$_3$ | OCH$_3$ | CH$_3$ | OCH$_3$ | |
| 4-SCH$_3$ | OCH$_3$ | CH$_3$ | OCH$_3$ | |
| 2-CO$_2$—i-C$_3$H$_7$ | OCH$_3$ | CH$_3$ | OCH$_3$ | |
| 2-CO$_2$—n-C$_6$H$_{13}$ | OCH$_3$ | CH$_3$ | OCH$_3$ | |
| 2-Cl | O—i-C$_3$H$_7$ | CH$_3$ | OCH$_3$ | |
| 2-Cl | O—n-C$_{12}$H$_{25}$ | CH$_3$ | OCH$_3$ | |
| 2-Cl | OCH$_2$CH=CH$_2$ | CH$_3$ | OCH$_3$ | |
| 2-Cl | OCH$_2$CH$_2$OCH$_3$ | CH$_3$ | OCH$_3$ | |

TABLE V-continued

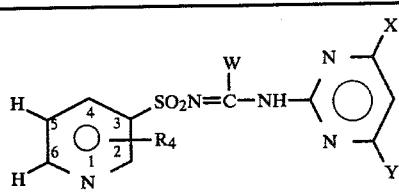

| R4 | W | X | Y | m.p. |
|---|---|---|---|---|
| 2-Cl | OCH2—(phenyl) | CH3 | OCH3 | |
| 2-Cl | OCH2CO2CH3 | CH3 | OCH3 | |
| 2-Cl | OCHCO2-i-C3H7 \| CH3 | CH3 | OCH3 | |
| 2-Cl | OCH3 | OCH3 | OCH3 | |
| 2-Cl | OCH3 | CH3 | OCH2CH3 | |
| 2-Cl | OCH3 | CH3 | O—n-C4H9 | |
| 2-Cl | OCH3 | CH3 | OCH2OCH3 | |
| 2-Cl | OCH3 | CH3 | O(CH2)3OCH3 | |
| 2-Cl | OCH3 | CH3 | OCH2CO2CH3 | |
| 2-Cl | OCH3 | CH3 | OCHCO2CH3 \| CH3 | |
| 2-Cl | OCH3 | CH3 | OCH2CCl3 | |
| 2-Cl | OCH3 | CH3 | OCH2CF3 | |
| H | OCH3 | CH3 | OCH3 | |
| H | Cl | CH3 | OCH3 | |

TABLE VI

| R4 | W | X | Y | m.p. |
|---|---|---|---|---|
| 2-Cl | Cl | CH3 | OCH3 | |
| 2-Cl | Br | CH3 | OCH3 | |
| 2-Cl | OCH3 | CH3 | OCH3 | |
| 4-Cl | OCH3 | CH3 | OCH3 | |
| 2-Br | OCH3 | CH3 | OCH3 | |
| 4-Br | OCH3 | CH3 | OCH3 | |
| 2-CH3 | OCH3 | CH3 | OCH3 | |
| 4-CH3 | OCH3 | CH3 | OCH3 | |
| 2-OCH3 | OCH3 | CH3 | OCH3 | |
| 4-OCH3 | OCH3 | CH3 | OCH3 | |
| 2-O(CH2)3CH3 | OCH3 | CH3 | OCH3 | |
| 2-NO2 | OCH3 | CH3 | OCH3 | |
| 4-NO2 | OCH3 | CH3 | OCH3 | |
| 2-CO2CH3 | OCH3 | CH3 | OCH3 | |
| 4-CO2CH3 | OCH3 | CH3 | OCH3 | |
| 2-SCH3 | OCH3 | CH3 | OCH3 | |
| 4-SCH3 | OCH3 | CH3 | OCH3 | |
| 2-CO2-i-C3H7 | OCH3 | CH3 | OCH3 | |
| 2-CO2-n-C6H13 | OCH3 | CH3 | OCH3 | |
| 2-Cl | O—i-C3H7 | CH3 | OCH3 | |
| 2-Cl | O—n-C12H25 | CH3 | OCH3 | |
| 2-Cl | OCH2CH=CH2 | CH3 | OCH3 | |
| 2-Cl | OCH2CH2OCH3 | CH3 | OCH3 | |
| 2-Cl | OCH2CH3 | CH3 | OCH3 | |

TABLE VII

| R4 | W | X | Y | m.p. |
|---|---|---|---|---|
| 2-Cl | OCH2CO2CH3 | CH3 | OCH3 | |
| 2-Cl | OCHCO2CH3 \| CH3 | CH3 | OCH3 | |
| 2-Cl | OCHCO2-i-C3H7 \| CH3 | CH3 | OCH3 | |
| 2-Cl | OCH3 | OCH3 | OCH3 | |
| 2-Cl | OCH3 | CH3 | OCH2CH3 | |
| 2-Cl | OCH3 | CH3 | O—n-C4H9 | |
| 2-Cl | OCH3 | CH3 | OCH2OCH3 | |
| 2-Cl | OCH3 | CH3 | O(CH2)3OCH3 | |
| 2-Cl | OCH3 | CH3 | OCH2CO2CH3 | |
| 2-Cl | OCH3 | CH3 | OCHCO2CH3 \| CH3 | |
| 2-Cl | OCH3 | CH3 | OCH2CCl3 | |
| 2-Cl | OCH3 | CH3 | OCH2CF3 | |
| H | OCH3 | CH3 | OCH3 | |
| H | Cl | CH3 | OCH3 | |

TABLE VIII

| R4 | W | A | Q | m.p. |
|---|---|---|---|---|
| 2-Cl | OCH3 | CH3O | —CH2— | |
| 2-Cl | OCH3 | CH3 | —O— | |

TABLE IX

| R4 | W | A | Q | m.p. |
|---|---|---|---|---|
| 2-Cl | OCH3 | CH3O | —CH2— | |
| 2-Cl | OCH3 | CH3 | —O— | |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.14 to 20% surfactant(s) and (b)

about 1% to 99.9% solid or liquid diluent(s). More specifically, they will contain these ingredients in the approximate proportions set forth in Table VI.

TABLE VI

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Solutions, Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agent's", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", Chemical Engineering, Dec. 4, 1967, pp. 147ff, and "Perry's Chemical Engineer's Handbook", 4th Ed., McGraw-Hill, New York, 1963, pp. 8–59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167, 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook". 5th Ed., Blackwell Scientific Publications, Oxford, 1968, pp. 101–103.

Unless indicated otherwise, all parts are by weight and temperatures in °C in the following examples.

EXAMPLE 4

| Extruded Pellet | |
|---|---|
| N'-(2-chlorophenylsulfonyl)-N-(4-methoxy-6-methyl-1,3,5-triazin-2-yl)carbamimidic acid, methyl ester. | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 5

| High Strength Concentrate | |
|---|---|
| N'-(2-chlorophenylsulfonyl)-N-(4-methoxy-6-methyl-1,3,5-triazin-2-yl)carbamimidic acid, methyl ester. | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 6

| Wettable Powder | |
|---|---|
| N'-(2-chlorophenylsulfonyl)-N-(4-methoxy-6-methyl-1,3,5-triazin-2-yl)carbamimidic acid, methyl ester. | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 7

| Granule | |
|---|---|
| wettable powder of Example 6 | 10% |
| attapulgite granules | 90% |

-continued

| Granule |
|---|
| (U.S.S. #20-40; 0.84-0.42 mm) |

A slurry of wettable powder containing 40% solids is sprayed on the surface of attapulgite granules in a double-cone blender. The granules are dried and packaged.

EXAMPLE 8

| Wettable Powder | |
|---|---|
| N'-(2-chlorophenylsulfonyl)-N-(4-methoxy-6-methyl-1,3,5-triazin-2-yl)carbamimidic acid, methyl ester. | 65% |
| dodecylphenyl polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended, sifted through a U.S.S. No. 50 sieve (0.3 mm opening) and packaged.

EXAMPLE 9

| Oil Suspension | |
|---|---|
| N'-(2-chlorophenylsulfonyl)-N-(4-methoxy-6-methyl-1,3,5-triazin-2-yl)carbamimidic acid, methyl ester. | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

UTILITY

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theathers, around billboards, highway and railroad structures. Alternatively, the subject compounds are useful for the selective pre- or post-emergence weed control in crops, such as wheat.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in the following greenhouse test. The test procedure and results follow.

TEST PROCEDURE A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated preemergence with a nonphytotoxic solvent solution of the compound in Table A. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), moringglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds in Table A. Other containers of the above-mentioned weeds and crops were treated pre- or post-emergence with the same nonphytotoxic solvent so as to provide a solvent control. A set of untreated control plants was also included for comparison. Preemergence and postemergence treated plants and controls were maintained in a greenhouse for sixteen days, then all treated plants were compared with their respective controls and rated visually for response to treatment, using the following symbols.

O=no effect
10=maximum effect
C=chlorosis or necrosis
D=defoliation
E=emergence inhibition
G=growth retardation
H=formative effects
U=usual pigmentation The data in Table A shows that the compounds of this invention are very effective herbicides.

TABLE A $$\begin{array}{c}CH_3\\ \diagdown\\ N\diagup\diagdown N\\ \|\quad\quad\diagdown NH-C=N-SO_2-\bigcirc\\ N\diagup\diagdown\quad\quad\|\quad\quad\quad\quad Cl\\ \diagdown N\quad\quad\quad OCH_3\\ CH_3O\end{array}$$

| kg/ha | 0.4 | 2 |
|---|---|---|
| POST-EMERGENCE | | |
| BUSHBEAN | 9D,9G,6Y | 9D,9G,6Y |
| COTTON | 5C,9G | 7C,9G |
| MORNINGGLORY | 9C | 10C |
| COCKLEBUR | 6G | 9C |
| CASSIA | 5C,9G | 9C |
| NUTSEDGE | 0 | 0 |
| CRABGRASS | 2C,4G | 3C,5G |
| BARNYARDGRASS | 5C,8H | 9C |
| WILD OATS | 0 | 2C |
| WHEAT | 0 | 1C |
| CORN | 2H,8G | 4U,9G |

TABLE A-continued

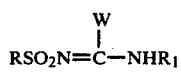

| kg/ha | 0.4 | 2 |
|---|---|---|
| SOYBEAN | 1C,9G | 1C,9G |
| RICE | 2C,8G | 3C,8G |
| SORGHUM | 2C,9G | 2C,9G |
| PRE-EMERGENCE | | |
| MORNINGGLORY | 9G | 9G |
| COCKLEBUR | 9G | 10B |
| CASSIA | 1C,9G | 1C,9G |
| NUTSEDGE | 0 | 5G |
| CRABGRASS | 0 | 1C |
| BARNYARDGRASS | 2C,7G | 3C,8G |
| WILD OATS | 0 | 3G |
| WHEAT | 0 | 3G |
| CORN | 1C,8G | 1C,9G |
| SOYBEAN | 9H | 9H |
| RICE | 7G | 9H |
| SORGHUM | 7G | 1C,8G |

What is claimed is:

1. A compound selected from compounds having the formula:

$$RSO_2N=C(W)-NHR_1$$

wherein

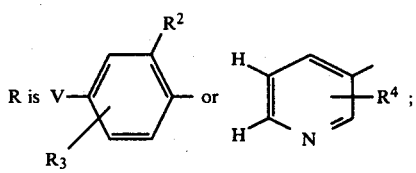

R is V—[phenyl with $R^2$, $R^3$] or [pyridyl with $R^4$];

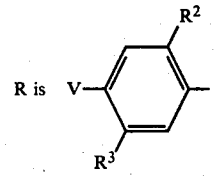

$R^1$ is [triazine/pyrimidine with X, Y, Z];

$R^2$ is $CH_3$, $OCH_3$, F, Cl, Br, $NO_2$, $CF_3$, $S(O)_mR^{10}$, where m is 0, 1 or 2, $COR^5$, or $SO_2NR^{10}R^{11}$;

$R^3$ is H, F, Cl, Br, $C_1$-$C_4$ alkyl, or $CH_3O$;

$R^4$ is Cl, Br, $CH_3$, $C_1$-$C_4$ alkoxy, $NO_2$, $CO_2R^6$, or $SCH_3$;

$R^5$ is $C_1$-$C_{10}$ alkoxy, $C_3$-$C_6$ alkenyloxy, $C_2$-$C_6$ alkoxy substituted with 1-3 halogens selected from F, Cl, or Br; $C_5$-$C_6$ cycloalkoxy, $OCH_2CH_2OR^7$, $O(CH_2)_3OR^7$, $C_1$-$C_4$ alkylthio, $NR^8R^9$ or $N(OCH_3)CH_3$;

$R^6$ is $C_1$-$C_6$ alkyl;

$R^7$ is $CH_3$ or $C_2H_5$;

$R^8$ and $R^9$ are independently $C_1$-$C_4$ alkyl, or $R^8R^9$ can be taken together to be $(CH_2)_5$, $(CH_2)_5$, or $O(CH_2CH_2-)_2$;

$R^{10}$ and $R^{11}$ are independently $C_1$-$C_6$ alkyl, $C_3$-$C_4$ alkenyl, or $R^{10}$ and $R^{11}$ can be taken together to be $(CH_2)_4$, $(CH_2)_5$, or $O(CH_2CH_2-)_2$;

V is H or F;

W is Cl, Br or $OR^{12}$;

$R^{12}$ is $C_1$-$C_{12}$ alkyl, $C_3$-$C_4$ alkenyl, $CH_2CH_2OCH_3$, $CH_2CH_2OCH_2CH_2$, $(CH_2)_3OCH_3$, benzyl, $CHR^{13}CO_2R^{14}$, where $R^{13}$ is H or $CH_3$ and $R^{14}$ is $C_1$-$C_4$ alkyl;

X is $CH_3$ or $OCH_3$;

Y is $CH_3$, $C_1$-$C_4$ alkoxy, $O(CH_2)_nOR^{15}$, where n is 1-3 and $R^{15}$ is $C_1$-$C_3$ alkyl; $OCHR^{16}CO_2R^{15}$, where $R^{16}$ is H or $CH_3$; $CF_3CH_2O$ or $CCl_3CH_2O$;

Z is N;

Q is $CH_2$ or O; and

A is $CH_3$ or $CH_3O$ and their agriculturally acceptable salts.

2. A compound of claim 1 wherein W is $OR^{12}$.

3. A compound of claim 2 wherein

R is V—[phenyl with $R^2$, $R^3$]

and V is H.

4. A compound of claim 3 wherein $R^2$ is Cl, $CH_3$, $OCH_3$, $COR^5$, $SO_2NR^{10}R^{11}$, $SO_2R^{10}$ or $NO_2$.

5. A compound of claim 4 wherein $R^3$ is H, Cl, $CH_3$ or $OCH_3$.

6. A compound of claim 5 wherein $R^2$ is Cl, $NO_2$, or $COR^5$, where $R^5$ is $C_1$-$C_3$ alkoxy or allyloxy.

7. The compound of claim 1, N'-(2-chlorophenylsulfonyl)-N-(4-methoxy-6-methyl-1,3,5-triazin-2-yl)-carbamimidic acid, methyl ester.

* * * * *